United States Patent [19]
Gololobov et al.

[11] Patent Number: 6,096,848
[45] Date of Patent: *Aug. 1, 2000

[54] PROCESS FOR THE PRODUCTION OF BISCYANOACRYLATES

[75] Inventors: Yuri Gololobov, Moscow, Russian Federation; Werner Gruber, Korschenbroich; Christian Nicolaisen, Ronnenberg, both of Germany

[73] Assignee: Henkel Kommanditgesellschaft auf Aktien, Duesseldorf, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/750,401
[22] PCT Filed: May 30, 1995
[86] PCT No.: PCT/EP95/02049
  § 371 Date: Mar. 5, 1997
  § 102(e) Date: Mar. 5, 1997
[87] PCT Pub. No.: WO95/33708
  PCT Pub. Date: Dec. 14, 1995

[30] Foreign Application Priority Data

Jun. 6, 1994 [DE] Germany .............. 44 19 740

[51] Int. Cl.[7] .................................................. C07C 253/30
[52] U.S. Cl. .................... 526/298; 526/297; 526/312; 558/303; 558/462; 560/155
[58] Field of Search ...................... 526/298, 312, 526/297; 558/303, 462; 560/155

[56] References Cited

U.S. PATENT DOCUMENTS 3,254,111  5/1966  Hawkins et al. ............. 260/465.4
3,654,340  4/1972  Banitt ....................... 260/465.4
3,975,422  8/1976  Buck ......................... 260/465.4

FOREIGN PATENT DOCUMENTS 1764554   8/1971  Germany .
2231561   1/1974  Germany .
0726086   4/1980  U.S.S.R. .
WO9415907 7/1994  WIPO .

OTHER PUBLICATIONS

Abstract of L.

Carl J. Buck, Journal of Polymer Science: Polymer Chemistry Edition, vol. 16, 2475–2507, 1978.

Gololobov, Yu. G., et al., "A Novel Approach to the Synthesis of bis(2–cyanoacrylates)", Russian Chemical Bulletin, vol. 42, No. 5, May 1993, p. 961.

Ullman's Encyclopedia of Industrial Chemistry, 5th ed., vol. A 1, Verlag Chemie, Weinheim, 1985; p. 240.ff. "6.2.1 Adhesives Setting by Polymerization", esp. col. 2.

*Primary Examiner*—Fred Zitomer
*Attorney, Agent, or Firm*—Wayne C. Jaeschke; Stephen D. Harper

[57] ABSTRACT

Biscyanoacrylates in solution are prepared by reacting 2-cyanoacrylic acids or their alkyl esters with diols in the presence of sulfonic acids as catalysts. The reaction mixture is processed by substituting an aliphatic solvent for the aromatic solvent and is then subjected twice to fractional crystallization. The thus obtained biscyanoacrylates are very pure. They are therefore useful for producing storage stable cyanoacrylate adhesives. Their admixture increases the thermal resistance of the adhesives, which is particularly important in the case of electric and electronic components.

19 Claims, No Drawings

PROCESS FOR THE PRODUCTION OF BISCYANOACRYLATES

FIELD OF THE INVENTION

This invention relates to a process for the production of biscyanoacrylates and to their use in cyanoacrylate adhesives.

BACKGROUND OF THE INVENTION

Biscyanoacrylates and their production have been known for some time. They are produced by at least the following two methods:

In the Knoevenagel condensation, formaldehyde is reacted with biscyanoacetates to form a crosslinked polymer which cannot readily be thermally depolymerized.

In the Retro-Diels-Alder reaction, a monofunctional cyanoacrylate is first blocked with dienes. The blocked monofunctional cyanoacrylate is hydrolyzed to the free acid. The ester is then prepared from the corresponding acid chloride with a diol. Finally, after the biscyanoacrylate has been exchanged for maleic anhydride, the pure biscyanoacrylate is obtained after repeated recrystallization from benzene. Accordingly, this method of production comprises five stages and is thus uneconomical.

DETAILED DESCRIPTION OF THE INVENTION

There is therefore a need for a simple method of producing pure biscyanoacrylate.

The solution provided by the invention is defined in the claims and essentially comprises transesterifying monocyanoacrylates with diols and working up the reaction mixture by fractional crystallization. The process according to the invention for the production of biscyanoacrylates is thus characterized in that 2-cyanoacrylic acid corresponding to the following general formula:

$$H_2C=C(CN)-CO-O-R^2 \quad (II)$$

in which $R^2$ is a branched or unbranched alkyl group containing 1 to 6 carbon atoms,
or an alkyl ester thereof is transesterified with diols corresponding to the following general formula:

$$[HO]_2R^1 \quad (III)$$

in which $R^1$ is a branched or unbranched difunctional alkane group containing 2 to 18 carbon atoms, which may also contain hetero atoms, such as halogens and oxygen, or aliphatic or aromatic rings,
to form biscyanoacrylates corresponding to the following general formula:

$$[H_2C=C(CN)-CO-O]_2R^1 \quad (I)$$

and the reaction mixture is subsequently purified by fractional crystallization.

Accordingly, one starting product is the monofunctional cyanoacrylic acid corresponding to formula II or an alkyl ester thereof. The alkyl group should be selected so that the alcohol formed is easy to remove. Possibilities suitable for this purpose are known to the expert from the general transesterification reaction. The alcohol is preferably removed by distillation. $R^2$ is therefore a branched or unbranched alcohol radical containing 1 to 6 carbon atoms and preferably 1 or 2 carbon atoms. The monofunctional cyanoacrylate is stabilized in the usual way.

The diols are dihydric primary or secondary alcohols, preferably primary alcohols. The hydroxyl groups may be in any position to one another, although they are preferably in the $\alpha/\omega$ position. The diols contain 2 to 18 carbon atoms and preferably 4 to 12 carbon atoms. They may be linear, branched or cyclic. The aliphatic radical may even be an aromatic group or, in addition to the hydrogen and carbon atoms, may also contain hetero atoms, for example chlorine or oxygen atoms, preferably in the form of polyethylene or polypropylene glycol units. Suitable diols are hexanediol, octanediol, decanediol and dodecanediol.

The cyanoacrylate is used in excess. The molar ratio of monofunctional cyanoacrylate to diol is therefore at least 2.0:1.0, preferably 2.5:1.0 and more preferably 2.2:1.0.

The transesterification is catalyzed by strong acids, more especially by sulfonic acids, preferably by aromatic sulfonic acids such as, for example, p-toluene sulfonic acid. However, naphthalene sulfonic acid and benzene sulfonic acid and acidic ion exchangers may also be used as transesterification catalysts. The concentration of the transesterification catalyst should be between 1 and 20% by weight, based on the monofunctional cyanoacrylate.

The transesterification is carried out in solution as is normally the case. Suitable solvents are aromatic hydrocarbons and halogenated hydrocarbons. The preferred solvent is toluene or xylene. The concentration of the solution is in the range from 10 to 50% and preferably in the range from 10 to 20%.

The monohydric alcohol formed and the water formed are removed in known manner, preferably being distilled off with the solvent. The conversion of the transesterification reaction is monitored, for example with the aid of NMR spectra. The reaction takes several hours as usual. Where toluene is used as the solvent and p-toluene sulfonic acid as the catalyst, the reaction is over after 10 to 15 hours, i.e. no more alcohol separates off.

The working up of the reaction mixture is very important. Where acidic ion exchangers are used as the catalyst, they may simply be filtered off. Where soluble sulfonic acids, for example p-toluene sulfonic acid, are used as the catalyst, they are removed by solvent substitution, i.e. toluene is replaced by a mixture of hexane, heptane or decane. Pure biscyanoacrylate is obtained after two fractional crystallizations. According to NMR spectra, the purity of the biscyanoacrylate exceeds 99%.

The biscyanoacrylate obtained is stable in storage with the usual stabilizers and in the usual concentrations, i.e. its melting point hardly changes after storage for 6 months at 20° C.

However, the biscyanoacrylates obtained polymerize very quickly in the presence of bases. As with monofunctional cyanoacrylates, traces of water are sufficient for this purpose. A three-dimensionally crosslinked polymer with relatively good thermal properties is formed.

Accordingly, it is preferably used in known cyanoacrylate adhesives in a quantity of 1 to 50% by weight and preferably in a quantity of 2 to 10% by weight, based on the adhesive as a whole.

Known cyanoacrylate adhesives contain as their principal component 2-cyanoacrylates corresponding to the following general formula:

$$H_2C=C(CN)-CO-O-R \quad (IV)$$

in which R is an alkyl, alkenyl, cycloalkyl, aryl, alkoxyalkyl, aralkyl or haloalkyl group, more particularly a methyl, ethyl, n-propyl, isopropyl, n-butyl, isobutyl, pentyl, hexyl, allyl, methallyl, crotyl, propargyl, cyclohexyl, benzyl, phenyl, cresyl, 2-chloroethyl, 3-chloropropyl, 2-chlorobutyl, trifluoroethyl, 2-methoxyethyl, 3-methoxybutyl and 2-ethoxyethyl group. The cyanoacrylates mentioned above are known to the expert on adhesives, cf. Ullmann's Encyclopaedia of Industrial Chemistry, Vol. A1, page 240, Verlag Chemie, Weinheim (1985) and U.S. Pat. No. 3,254,111 and U.S. Pat. No. 3,654,340. Preferred monomers are the allyl, methoxyethyl, ethoxyethyl, methyl, ethyl, propyl or butyl esters of 2-cyanoacrylic acid.

The adhesive may contain additives, for example plasticizers, thickeners, stabilizers, activators, dyes, etc.

The new cyanoacrylate adhesive according to the invention is particularly suitable for bonds which are expected to satisfy stringent thermal requirements, for example for the bonding of electrical and electronic components.

The invention is illustrated by the following Examples.

EXAMPLE 1

I. Production of biscyanoacrylates

Using the general production process described in the foregoing, the starting products listed in Table 1 were reacted in 1 kg of toluene in the presence of p-toluene sulfonic acid as catalyst. The transesterification was over after 6 hours. The toluene was then replaced by hexane. The corresponding biscyanoacrylates with the melting points shown in the Table were obtained after two fractional crystallizations.

TABLE 1

| No. | Starting Products | a) 1.0:0.5 Quantities in g | b) 1.2:0.4 Quantities in g | Melting Point ° C. |
|---|---|---|---|---|
| 1. | Methyl cyanoacrylate | 65.96 | 69.99 | 59–60 |
|  | Hexane-1,6-diol | 35.05 | 27.68 |  |
| 2. | Methyl cyanoacrylate | 60.92 | 65.24 | 65–67 |
|  | Octane-1,8-diol | 40.08 | 35.76 |  |
| 3. | Methyl cyanoacrylate | 56.63 | 61.10 | 74–75 |
|  | Decane-1,10-diol | 44.38 | 39.91 |  |
| 4. | Methyl cyanoacrylate | 52.89 | 57.45 | 79–80 |
|  | Dodecane-1,12-diol | 48.12 | 43.56 |  |

EXAMPLE 2

II. Use of the biscyanoacrylates in cyanoacrylate adhesives

A few drops of the cyanoacrylate adhesive based on ethyl cyanoacrylate with the indicated additions of biscyanoacrylates were applied to the cleaned (blasted) aluminium or steel plates and cured for 24 hours at 20° C. The bonded plates were then stored for 3 days at 20, 100 and 150° C. and tested for strength at those temperatures.

TABLE 2

Tensile Shear Strength (m N/mm$^2$)

| | Biscyanoacrylates | | | Tensile shear strength | | |
|---|---|---|---|---|---|---|
| No. | Type | Quantity [%] | Substrate | 20° C. | 100° C. | 150° C. |
| 1 a) | — | 0 | Steel |  | 5 | 3 |
| b) | — | 0 | Al |  | 6 | 2 |
| 2 | Hexanediol biscyanoacrylate | 5 | Steel | 21 | 18 | 12 |
| 3 | Octandiol | 10 | Al | 18 | 16 | 10 |

What is claimed is:

1. A process for the production of a biscyanoacrylate corresponding to the following general formula:

$$[H_2C=C(CN)-CO-O]_2R^1 \quad (I)$$

wherein R$^1$ is the residue of a diol, which comprises the steps of:

esterifying a 2-cyanoacrylic acid or transesterifying an alkyl ester thereof corresponding to the following general formula:

$$H_2C=C(CN)-CO-O-R^2 \quad (II)$$

in which R$^2$ is selected from the group consisting of hydrogen and branched and unbranched alkyl groups containing 1 to 6 carbon atoms with a diol corresponding to the following general formula:

$$[HO]_2R^1 \quad (III)$$

to obtain a reaction mixture; and fractionally crystallizing the reaction mixture to obtain the biscyanoacrylate.

2. The process of claim 1, wherein the diol residue R$^1$ is selected from the group consisting of branched and unbranched difunctional alkane residues containing from about 2 to about 18 carbon atoms, said alkane residues optionally also containing heteroatoms or aliphatic or aromatic rings.

3. The process of claim 2, wherein the
heteroatoms are selected from the group consisting of oxygen and halogens and mixtures thereof.

4. The process of claim 2, wherein the heteroatoms are in the form of units selected from the group consisting of polyethylene glycol and polypropylene glycol and mixtures thereof.

5. The process of claim 1, wherein the diol is selected from the group consisting of hexanediol, octanediol decanediol, and dodecanediol.

6. The process of claim 1, wherein R$^2$ is an alkyl group containing 1 or 2 carbon atoms.

7. The process of claim 1, wherein the esterification or transesterification is carried out in the presence of a sulfonic acid in a concentration of 1 to 20% by weight, based on the 2-cyanoacrylic acid or alkylester thereof.

8. The process of claim 7, wherein the sulfonic acid is toluene sulfonic acid.

9. The process of claim 7, wherein the sulfonic acid is selected from the group consisting of naphthalene sulfonic acid, benzene sulfonic acid, acidic ion exchangers and mixtures thereof.

10. The process of claim 1, wherein the esterification or transesterification step further comprises a solvent selected from the group consisting of toluene and xylene and mixtures thereof.

11. The process of claim 1, wherein the fractional crystallization step further comprises a solvent selected from the group consisting of hexane, heptane and decane and mixtures thereof.

12. The process of claim 1, wherein the molar ratio of 2-cyanoacrylic acid or alkyl ester thereof to diol is at least about 2.0:1.0.

13. The process of claim 1, wherein the molar ratio of 2-cyanoacrylic acid or alkyl ester thereof to diol is at least about 2.2:1.0.

14. A process for the production of
a biscyanoacrylate corresponding to the following general formula:

$$[H_2C=C(CN)-CO-O]_2R^1 \quad (I)$$

wherein R$^1$ is the residue of a diol, which comprises the steps of:

esterifying a 2-cyanoacrylic acid or transesterifying an alkyl ester thereof corresponding to the following general formula:

$$H_2C=C(CN)-CO-O-R^2 \quad (II)$$

in which $R^2$ is selected from the group consisting of hydrogen and branched and unbranched alkyl groups containing 1 to 6 carbon atoms in the presence of a strong acid catalyst and in the presence of a solvent selected from the group consisting of aromatic hydrocarbons and halogenated hydrocarbons and mixtures thereof with a diol corresponding to the following general formula:

$$[HO]_2R^1 \qquad (III)$$

to obtain a reaction mixture; and fractionally crystallizing the reaction mixture in a solvent selected from the group consisting of hexane, heptane and decane and mixtures thereof biscyanoacrylate.

15. A process for the production of a biscyanoacrylate corresponding to the following general formula:

$$[H_2C=C(CN)-CO-O]_2R^1 \qquad (I)$$

wherein $R^1$ is the residue of a dial selected from the group consisting of hexane-1,6-dial, octane-1,8-diol, decane-1,10-diol, dodecane-1,12-diol and mixtures thereof which comprises the steps of:

transesterifying an alkylester of a 2-cyanoacrylic acid corresponding to the following general formula:

$$H_2C=C(CN)-CO-O-R^2 \qquad (II)$$

in which $R^2$ is selected from the group consisting of branched and unbranched alkyl groups containing 1 to 6 carbon atoms in the presence of about 1 to about 20 wt. % soluble sulfonic acid catalyst and in the presence of a solvent selected from the group consisting of toluene and xylene and mixtures thereof with a diol selected from the group consisting of hexane-1,6-diol, octane-1,8-diol, decane-1,10-diol, dodecane-1,12-diol and mixtures thereof to obtain a reaction mixture; and fractionally crystallizing the reaction mixture in a solvent selected from the group consisting of hexane, heptane and decane and mixtures thereof to obtain the biscyanoacrylate.

16. A method of preparing a cyanoacrylate adhesive, comprising combining one or more biscyanoacrylates produced by the process of claim 1 in a quantity of 1 to 50% by weight, based on the cyanoacrylate adhesive, with one or more 2-cyanoacrylates corresponding to the general formula $$H_2C=C(CN)-CO-O-R$$

wherein R is selected from the group consisting of alkyl, alkenyl, cycloalkyl, aryl, alkoxyalkyl, aralkyl and haloalkyl groups and, optionally, one or more additives selected from the group consisting of plasticizers, thickeners, stabilizers, activators and dyes.

17. The method of claim 16 wherein the 2-cyanoacrylates are selected from the group consisting of alkyl, methoxyethyl, ethoxyethyl, methyl, ethyl, propyl and butyl esters of 2-cyanoacrylic acid.

18. The method of claim 16 wherein the quantity of biscyanoacrylates is from 2 to 10% by weight, based on the cyanoacrylate adhesive.

19. A method of preparing a cyanoacrylate adhesive, comprising combining one or more biscyanoacrylates produced by the process of claim 14 in a quantity of 2 to 10% by weight, based on the cyanoacrylate adhesive, with one or more cyanoacrylates selected from the group consisting of alkyl, methoxyethyl, ethoxyethyl, methyl, ethyl, propyl and butyl esters of 2-cyanoacrylic acid and, optionally, one or more additives selected from the group consisting of plasticizers, thickeners, stabilizers, activators and dyes.

* * * * *